United States Patent
El-Gamal et al.

(10) Patent No.: US 10,278,999 B2
(45) Date of Patent: *May 7, 2019

(54) **SYNTHESIS OF *NUXIA OPPOSITIFOLIA* NANOPARTICLES**

(71) Applicant: KING SAUD UNIVERSITY, Riyadh (SA)

(72) Inventors: Ali Ali El-Gamal, Riyadh (SA); Adnan Jathlan Al-Rehaily, Riyadh (SA); Manal Ahmed Gasmelseed Awad, Riyadh (SA); Rabab Abd El Moneim Khalil El Dib, Riyadh (SA); Shaza Mohamed Adel Al-Massarani, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/826,018

(22) Filed: Nov. 29, 2017

(65) Prior Publication Data

US 2018/0344789 A1 Dec. 6, 2018

Related U.S. Application Data

(63) Continuation-in-part of application No. 15/611,768, filed on Jun. 1, 2017, now Pat. No. 10,028,988.

(51) Int. Cl.
*A61K 36/185* (2006.01)

(52) U.S. Cl.
CPC ........ *A61K 36/185* (2013.01); *A61K 2236/33* (2013.01); *A61K 2236/35* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 4,826,689 A | 5/1989 | Violanta et al. | |
| 6,623,761 B2 | 9/2003 | Hassan | |
| 8,852,644 B2 | 10/2014 | Baumstuemmler et al. | |

FOREIGN PATENT DOCUMENTS

| | | | |
|---|---|---|---|
| JP | 020092134 A | * | 9/2009 |
| RU | 2494754 C1 | | 10/2013 |

OTHER PUBLICATIONS

Al-Massarani et al. (New Cytotoxic Seco-type Triterpene and Labdane-Type Dlterpenes from Nuxia oppositifolia, Molecules, 22, Mar. 29, 2017).*

(Continued)

*Primary Examiner* — Christopher R Tate
(74) *Attorney, Agent, or Firm* — Richard C. Litman

(57) ABSTRACT

In one embodiment, synthesis of *Nuxia oppositifolia* nanoparticles includes providing a *Nuxia oppositifolia* powder; dissolving the powder in a first alcohol to provide a first alcohol extract; concentrating a filtrate from the first alcohol extract under reduced pressure to provide a dried alcohol extract; dissolving the dried alcohol extract in the first alcohol to provide a second alcohol extract; successively partitioning the second alcohol extract using n-hexane to provide an n-hexane extract; dissolving the n-hexane extract in a second alcohol and water to provide a first solution; and adding an acidic solution to the first solution to form a final solution including *Nuxia oppositifolia* nanoparticles.

4 Claims, 9 Drawing Sheets

(56) References Cited

OTHER PUBLICATIONS

Viable Herbal Solutions (the cited website of http://web/archive.org/web/200000124113842/http;//viable-herbal.com/herbology/herbs42, copyrighted 1996-2000).*

Al-Massarani et al., "New Cytotoxic Seco-Type Triterpene and Labdane-Type Diterpenes from Nuxia oppositifolia," Molecules, 22, 389, Mar. 2017.

* cited by examiner

SYNTHESIS OF *NUXIA OPPOSITIFOLIA* NANOPARTICLES

CROSS-REFERENCE TO RELATED APPLICATION

This application is a continuation-in-part of U.S. application Ser. No. 15/611,768 filed Jun. 1, 2017.

BACKGROUND

1. Field

The disclosure of the present patent application relates to nanoparticle synthesis, and particularly to a synthesis of *Nuxia oppositifolia* nanoparticles.

2. Description of the Related Art

Nanoparticles exhibit completely new properties compared to their corresponding bulk materials. Nanoparticles have found tremendous application in the fields of drug delivery for water insoluble compounds, high sensitivity bimolecular detection and diagnostics, therapeutics, antimicrobials, and nanomedicine.

The genus *Nuxia* (family Buddlejaceae) includes about fifteen species of shrubs and trees spread over the Arabian peninsula, tropical and South Africa. It has been found that the dichloromethane leaf extract of *N. verticillata*, endemic to the Mascarene Archipelago, has potential anti-proliferative activity ($IC_{50}$=44 ug/ml) and selectively inhibits cancer cell growth in comparison with normal cells.

*Nuxia* is represented in Saudi Arabia by two species, *N. oppositifolia* and *N. congesta*, which grow in the forests below the juniper zone, usually in riverine habitats. Many *Nuxia* species are plants of economic and medicinal interest with a rich diversity of ethnobotanical uses. Leaves of *N. floribunda* are reported to be used for infantile convulsions in parts of Africa. *Nuxia oppositifolia* (Hochst.) Benth., known as Water elder, is an ever green shrub. In the traditional medicine of southern Africa, the smoke of the burning leaves of *Nuxia oppositifolia* is inhaled to treat headache. In Madagascar, *Nuxia oppositifolia* leaf decoction is used to treat malaria in children.

Thus, a synthesis of *Nuxia oppositifolia* nanoparticles solving the aforementioned problems is desired.

SUMMARY

In one embodiment, synthesis of *Nuxia oppositifolia* nanoparticles includes providing an extract of *Nuxia oppositifolia*, dissolving the extract in alcohol to provide a mixture, adding water to the mixture to provide an aqueous solution, adding an acidic solution to the aqueous solution to form a final solution including *Nuxia oppositifolia* nanoparticles; and centrifuging the final solution to isolate the *Nuxia oppositifolia* nanoparticles.

In another embodiment, synthesis of *Nuxia oppositifolia* nanoparticles includes providing a *Nuxia oppositifolia* powder; macerating the powder in a first alcohol to provide a first alcohol extract; concentrating a filtrate from the first alcohol extract under reduced pressure to provide a dried alcohol extract; dissolving the dried alcohol extract in the first alcohol to provide a second alcohol extract; successively partitioning the second alcohol extract using n-hexane to provide an n-hexane extract; dissolving the n-hexane extract in a second alcohol and water to provide a first solution; and adding an acidic solution to the first solution to form a final solution including *Nuxia oppositifolia* nanoparticles.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
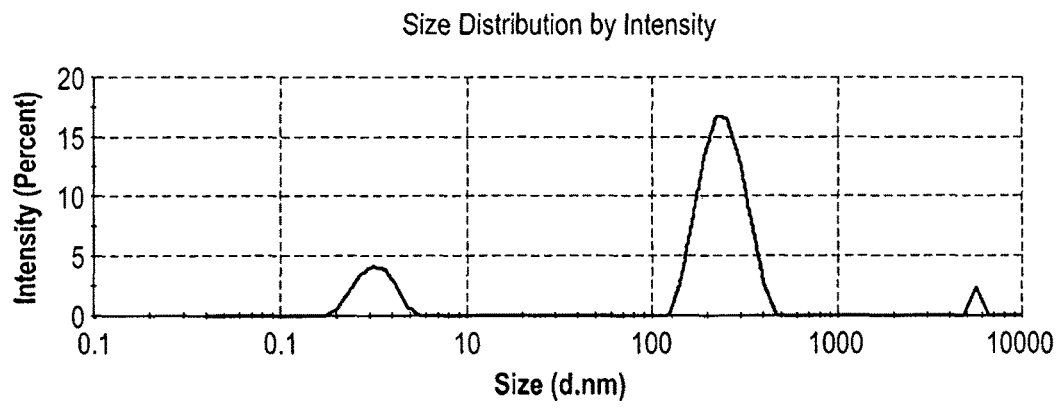
FIG. 1 is a graph showing the particles size distribution of *Nuxia oppositifolia* nanoparticles synthesized according to Example 1 of the present disclosure.

According to an embodiment, synthesis of *Nuxia oppositifolia* nanoparticles includes providing an extract of

*Nuxia oppositifolia*, dissolving the extract in alcohol to provide a mixture, adding water to the mixture to provide an aqueous solution, adding an acidic solution to the aqueous solution to form a final solution including *Nuxia oppositifolia* nanoparticles; and centrifuging the final solution to isolate the *Nuxia oppositifolia* nanoparticles. The extract can be a dried extract. The alcohol can be methanol. The acidic solution can be hydrochloric acid solution, e.g., 38% hydrochloric acid solution. The acidic solution can be added dropwise to the aqueous solution while stirring at a temperature of about 30±2° C. The final solution can be centrifuged at about 9000 rpm for about fifteen minutes.

According to an alternate embodiment, synthesis of *Nuxia oppositifolia* nanoparticles includes providing a *Nuxia oppositifolia* powder; macerating the powder in a first alcohol to provide a first alcohol extract; concentrating a filtrate from the first alcohol extract under reduced pressure to provide a dried alcohol extract; dissolving the dried alcohol extract in the first alcohol to provide a second alcohol extract; successively partitioning the second alcohol extract using n-hexane to provide an n-hexane extract; dissolving the n-hexane extract in a second alcohol and water to provide a first solution; and adding an acidic solution to the first solution to form a final solution including *Nuxia oppositifolia* nanoparticles. The first alcohol can be ethanol. The second alcohol can be methanol. The acidic solution can be hydrochloric acid solution, e.g., 38% hydrochloric acid solution. The acidic solution can be added dropwise to the aqueous solution while stirring at a temperature of about 30±2° C. The final solution can be centrifuged at about 9000 rpm for about fifteen minutes.

The *Nuxia oppositifolia* powder can be prepared from dried aerial parts, e.g., leaves and stems, of the *Nuxia oppositifolia* plant. The powder can be macerating with alcohol, e.g., 70% ethanol, at room temperature to provide the first alcohol extract. The resulting first alcohol extract of *Nuxia oppositifolia* can be filtered and concentrated under reduced pressure, e.g., at 40° C. using a rotary evaporator, to provide a dried extract of *Nuxia oppositifolia*. The dried extract can be redissolved in alcohol, e.g., 30% ethanol, and partitioned successively, several times with n-hexane, chloroform, and n-butanol, to provide corresponding n-hexane, chloroform, and n-butanol extracts.

The *Nuxia oppositifolia* nanoparticles can be used to effectively treat cancer. An effective amount of the *Nuxia oppositifolia* nanoparticles can be administered to a patient with cancer. The *Nuxia oppositifolia* nanoparticles can be used in combination with one or more additional treating agents for cancer. The cancer can include at least one of cervical cancer, lung cancer, breast cancer, liver cancer, and colon cancer.

The following examples illustrate the present teachings.

Example 1

Synthesis of *Nuxia oppositifolia* Nanoparticles from *N. oppositifolia* Dried Ethanolic Extract The fresh aerial parts (leaves and stems) of *Nuxia oppositifolia* were collected from Wadi Lajab in Jizan, located in the south part of Saudi Arabia. The plant was deposited at the Herbarium of the College of Pharmacy, King Saud University, Riyadh, Saudi Arabia.

The air-dried and powdered aerial parts of *N. oppositifolia* (500 g) were extracted by maceration with 70% ethanol (5×1 L) at room temperature. The combined obtained ethanolic extract was filtered and concentrated under reduced pressure at 40° C. using a rotary evaporator, to give a dried ethanolic extract (35 g).

Three grams of *N. oppositifolia* dried ethanolic extract were dissolved in 50 mL methanol under stirring, then 5 ml distilled water was added. After that a specific amount of 38% hydrochloric acid solution was added drop wise. The flask was kept under stirring at a temperature of 30±2° C. The *N. oppositifolia* nanoparticles were centrifuged (9000 rpm) for 15 minutes to collect the nanoparticles.

Figure 2A:
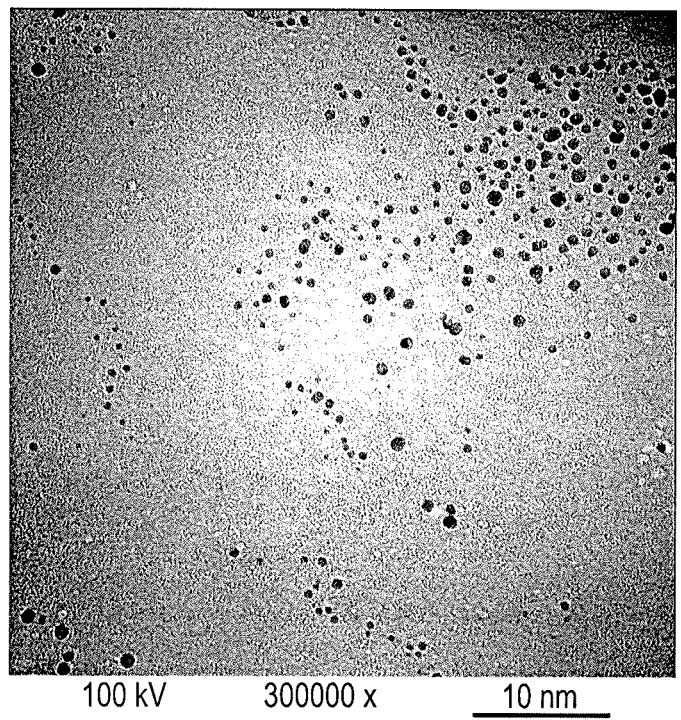
FIGS. 2A-2B are TEM images of the *Nuxia oppositifolia* nanoparticles synthesized according to Example 1 of the present disclosure.
Figure 2B:
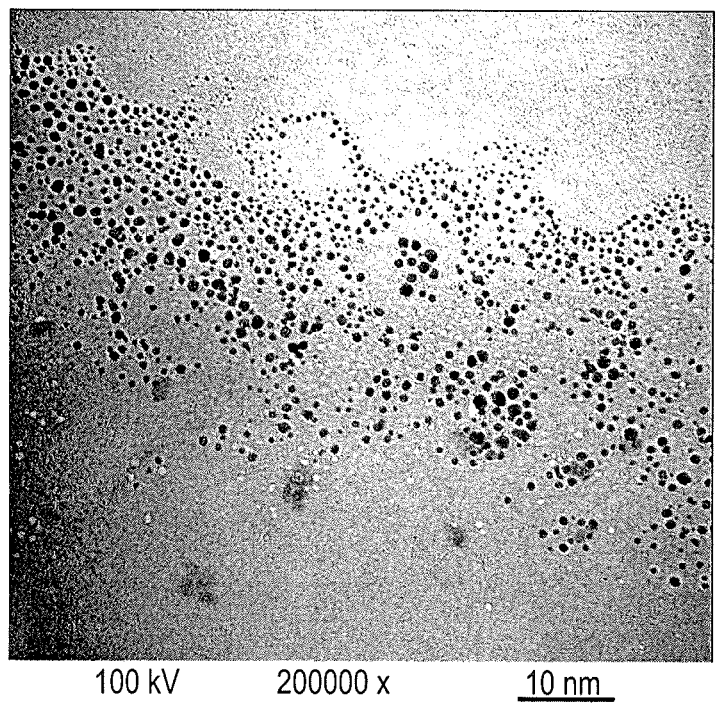

The synthesized nanoparticles were characterized using Zetasizer, Nano series, HT Laser, ZEN3600 from Molvern Instrument, UK to determine the average size of the resulting nanoparticles. Transmission electron microscopy (TEM, JEM-1400, JEOL, Japan) was employed to characterize the size, shape and morphologies of nanoparticles. FIG. 1 shows the particle size distribution of the *Nuxia oppositifolia* nanoparticles, with the Z-average particle size being 287 nm. FIGS. 2A-2B show TEM images of the *Nuxia oppositifolia* nanoparticles.

Example 2

Synthesis of *Nuxia oppositifolia* Nanoparticles from *N. oppositifolia* n-Hexane Extract The fresh aerial parts (leaves and stems) of *Nuxia oppositifolia* were collected from Wadi Lajab in Jizan, located in the south part of Saudi Arabia. The plant was deposited at the Herbarium of the College of Pharmacy, King Saud University, Riyadh, Saudi Arabia.

The air-dried and powdered aerial parts of *N. oppositifolia* (500 g) were extracted by maceration with 70% ethanol (5×1 L) at room temperature. The combined obtained ethanolic extract was filtered and concentrated under reduced pressure at 40° C. using a rotary evaporator to provide a dried ethanolic extract (35 g).

The dried ethanolic extract (35 g) was subsequently redissolved in 30% ethanol (200 mL) and partitioned successively several times with n-hexane (3×200 mL), chloroform (3×200 mL) and n-butanol (3×200 mL) to provide the corresponding extracts.

Five grams of the sticky residue of *N. oppositifolia* n-hexane extract were weighed and dissolved in 20-50 mL methanol under stirring, then 3-5 mL distilled water was added. After that, a specific amount of 38% hydrochloric acid solution was added dropwise. The flask was kept under stirring at a speed of 1000 rpm at a temperature of 30±2° C. The contents were centrifuged (9000 rpm) for 15 minutes to yield the formed nanoparticles.

Figure 8:
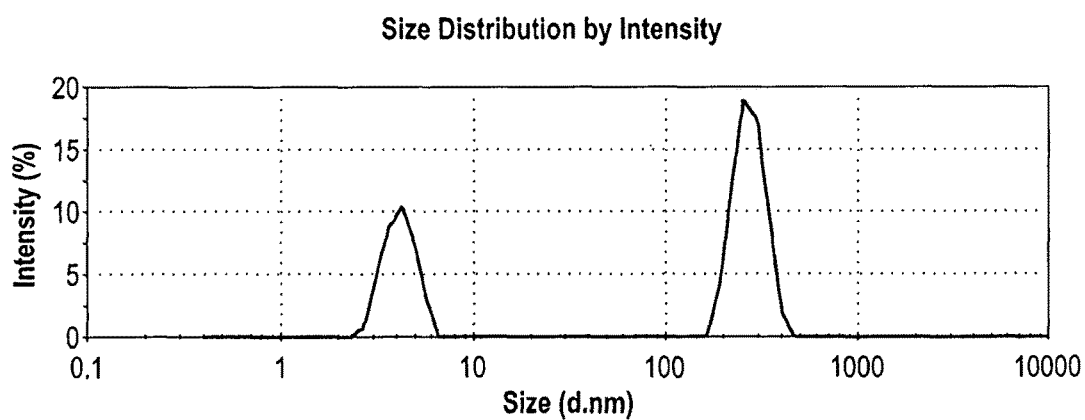
FIG. 8 is a graph showing the particle size distribution of the *Nuxia oppositifolia* nanoparticles synthesized according to Example 2 of the present disclosure.
Figure 9A:
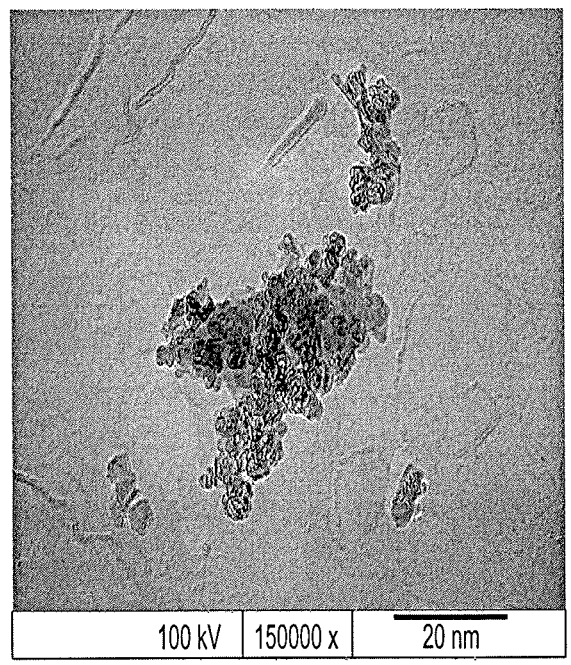
FIG. 9A is a TEM image of the *Nuxia oppositifolia* nanoparticles synthesized according to Example 2 of the present disclosure.
Figure 9B:
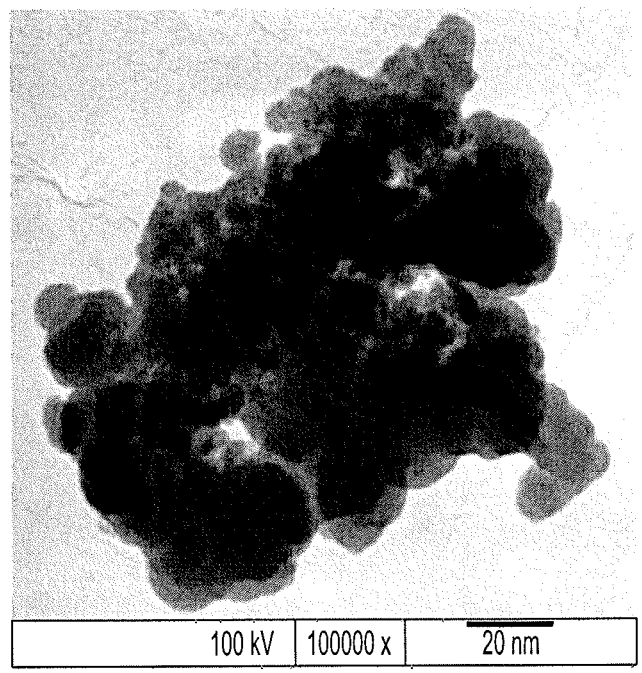
FIG. 9B is a TEM image of the *Nuxia oppositifolia* nanoparticles synthesized according to Example 2 of the present disclosure.

The synthesized nanoparticles were characterized using Zetasizer, Nano series, HT Laser, ZEN3600 from Molvern Instrument, UK to determine the average size of the resulting nanoparticles. Transmission electron microscopy (TEM, JEM-1400, JEOL, Japan) was employed to characterize the size, shape and morphologies of nanoparticles. FIG. 8 shows the particle size distribution of the *Nuxia oppositifolia* nanoparticles from *N. oppositifolia* n-hexane extract, with the particle size ranging from about 10 nm to about 200 nm. FIGS. 9A-9B show TEM images of the *Nuxia oppositifolia* nanoparticles.

Example 3

Cytotoxicity Evaluation of *Nuxia oppositifolia* Nanoparticles

Dimethyl sulfoxide (DMSO), crystal violet and trypan blue dye were purchased from Sigma (St. Louis, Mo., USA).

Fetal Bovine serum, DMEM, RPMI-1640, HEPES buffer solution, L-glutamine, gentamycin and 0.25% Trypsin-EDTA were purchased from (Bio Whittaker® Lonza, Belgium).

Crystal violet, composed of 0.5% (w/v) crystal violet and 50% methanol, was used as staining solution. The mammalian cell lines for HepG2 cells (human cell line of a well differentiated hepatocellular carcinoma isolated from a liver biopsy of a male Caucasian aged 15 years) were obtained from the American Type Culture Collection (ATCC), while the MCF-7 cells (human breast cancer cell line) were obtained from VACSERA Tissue Culture Unit.

The cells were propagated in Dulbeccos modified Eagles Medium (DMEM) supplemented with 10% heat inactivated fetal bovine serum, 1% L-glutamine, HEPES buffer and 50 µg/mL gentamicin. Cells were maintained at 37° C. in a humidified atmosphere with 5% CO2 and were sub-cultured two times a week.

The cytotoxic activity was evaluated by the crystal violet staining (CVS) method. Saotome K., Morita, H., and Umeda, M. (1989). "Cytotoxicity test with simplified crystal violet staining method using microtitre plates and its application to injection drugs." *Toxicol. In Vitro*, 3: 317-321.

Briefly, the cells were seeded in a 96-well tissue culture microplate, at a concentration of 1×104 cells per well in 100 µL of growth medium at 37° C. After 24 hours of seeding, fresh medium containing various concentrations of the tested compounds (50 µg, 25 µg, 12.5 µg, 6.25 µg, 3.125 µg & 1.56 µg) were added to the microtiter plates (each compound was tested in triplicate in all concentrations). Next, the microtiter plates were incubated at 37° C. in a humidified incubator with 5% $CO_2$. Control cells were incubated without test sample and with or without DMSO. The little percentage of DMSO present in the wells was found not to affect the experiment. After 48 hours incubation period, viable cells yield was determined by a colorimetric method.

In brief, media were aspirated for 30 min and the crystal violet solution (1%) was added to each well. The plates were rinsed after removing the stain by distilled water. Glacial acetic acid (30%) was then added to all wells and mixed thoroughly. The quantitative analysis, to evaluate the fixed cells, was performed calorimetrically by measuring the absorbance in an automatic Microplate reader (TECAN, Inc.) at 595 nm. The effect on cell growth was calculated as the difference in absorbance percentage in the presence and absence of the tested compounds. As discussed further below, a dose-response curve was plotted to acquire the concentration at which the growth of cells was inhibited to 50% of the control ($IC_{50}$). The standard antitumor drug used was doxorubicin.

Figure 3:
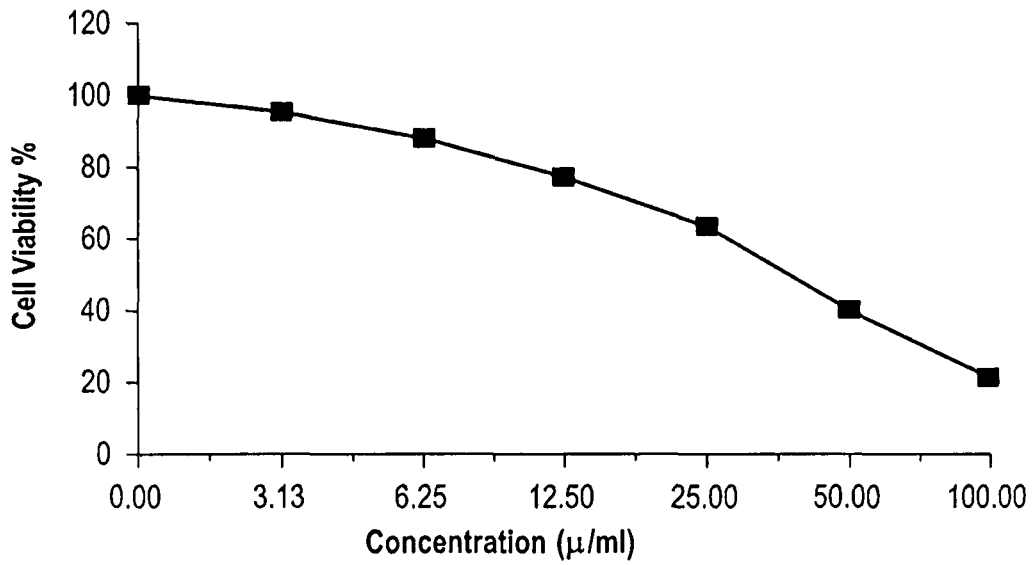
FIG. 3 is a graph showing the cytotoxicity of the *Nuxia oppositifolia* nanoparticles synthesized according to Example 1 of the present disclosure against HeLa cell line.
Figure 4:
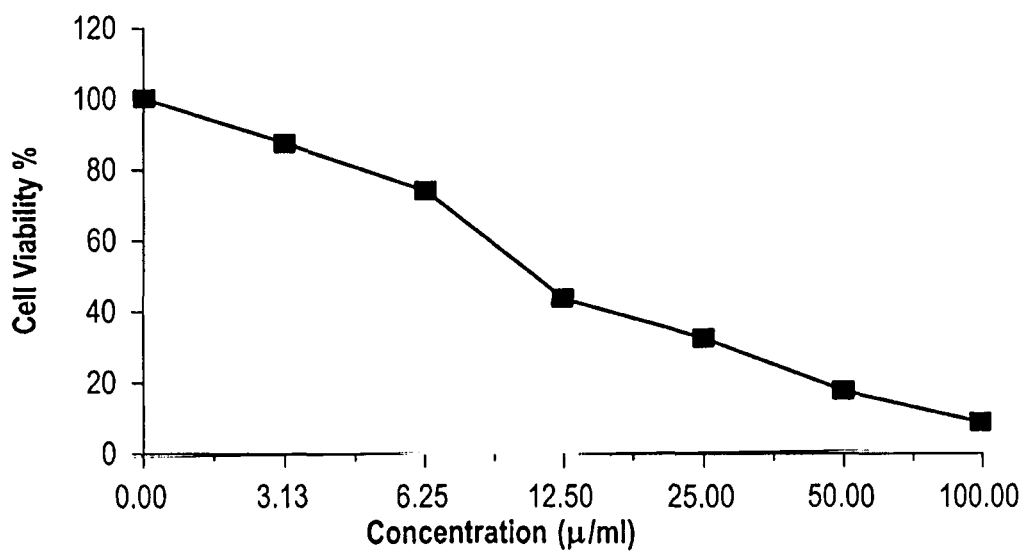
FIG. 4 is a graph showing the cytotoxicity of the *Nuxia oppositifolia* nanoparticles synthesized according to Example 1 of the present disclosure against A-549 cell line.
Figure 5:
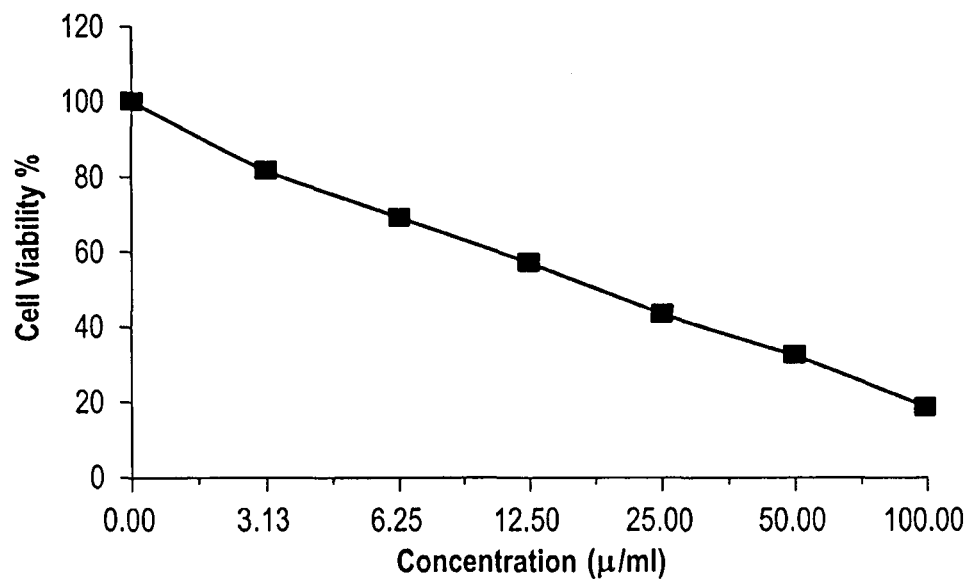
FIG. 5 is a graph showing the cytotoxicity of the *Nuxia oppositifolia* nanoparticles synthesized according to Example 1 of the present disclosure against MCF7 cell line.
Figure 6:
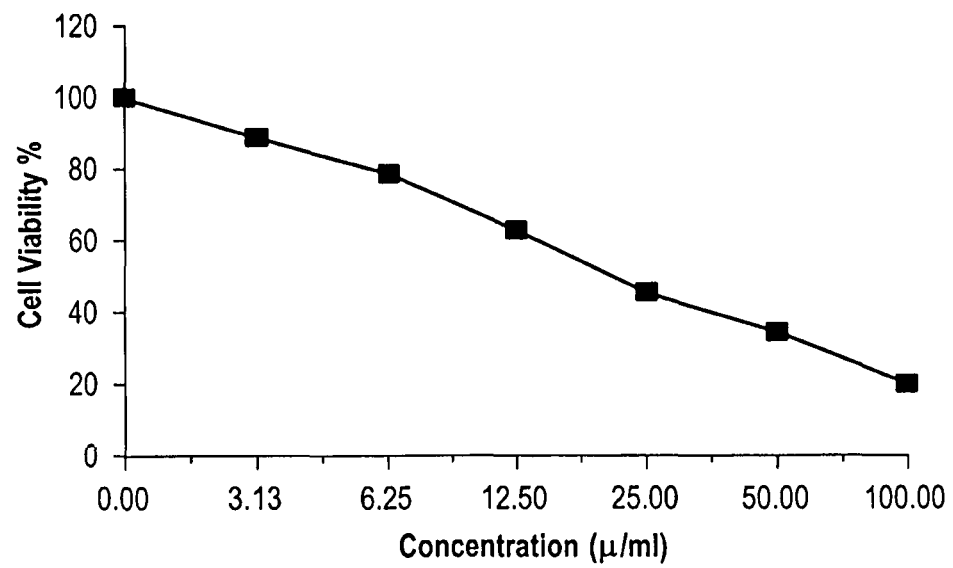
FIG. 6 is a graph showing the cytotoxicity of the *Nuxia oppositifolia* nanoparticles synthesized according to Example 1 of the present disclosure against HepG-2 cell line.
Figure 7:
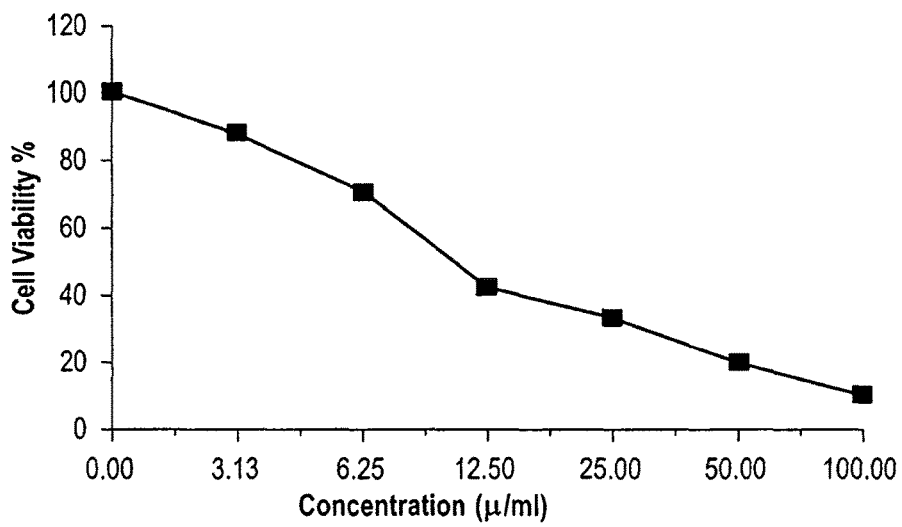
FIG. 7 is a graph showing the cytotoxicity of the *Nuxia oppositifolia* nanoparticles synthesized according to Example 1 of the present disclosure against HCT-116 cell line.

The cytotoxic effects of the nanoparticles synthesized according to Example 1 were evaluated against the five cancer cell lines, namely the cervical carcinoma cells HELA (FIG. 3, Table 1), the human lung adenocarcinoma epithelial cell line A549 (FIG. 4, Table 2), the breast carcinoma cells MCF-7 (FIG. 5, Table 3), the hepatocellular carcinoma cells HepG-2 (FIG. 6, Table 4) and the human colon carcinoma cells HCT-116 (FIG. 7, Table 5). The results, provided in Tables 1-5 and FIGS. 3-7, indicate that the *N. oppositifolia* nanoparticles are effective in inhibiting cancer cells.

TABLE 1

Evaluation of cytotoxicity of synthesized *N. oppositifolia* nanoparticles against HeLa cell line with $IC_{50}$ = 39.7 µl/ml.

| Sample conc. (µl/ml) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 24.87 | 18.68 | 21.85 | 21.80 | 78.20 | 3.10 |
| 50 | 41.92 | 38.74 | 40.72 | 40.46 | 59.54 | 1.61 |
| 25 | 63.84 | 64.89 | 61.95 | 63.56 | 36.44 | 1.49 |
| 12.5 | 79.68 | 78.91 | 74.18 | 77.59 | 22.41 | 2.98 |
| 6.25 | 86.19 | 89.47 | 88.96 | 88.21 | 11.79 | 1.77 |
| 3.125 | 94.02 | 97.24 | 95.17 | 95.48 | 4.52 | 1.63 |

TABLE 2

Evaluation of cytotoxicity of synthesized *N. oppositifolia* nanoparticles against A-549 cell line with $IC_{50}$ = 11.2 µl/ml.

| Sample conc. (µl/ml) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 7.38 | 10.12 | 9.58 | 9.03 | 90.97 | 1.45 |
| 50 | 18.04 | 19.73 | 16.46 | 18.08 | 81.92 | 1.64 |
| 25 | 32.56 | 34.64 | 30.83 | 32.68 | 67.32 | 1.91 |
| 12.5 | 43.25 | 46.51 | 41.92 | 43.89 | 56.11 | 2.36 |
| 6.25 | 78.72 | 69.65 | 73.41 | 73.93 | 26.07 | 4.56 |
| 3.125 | 90.21 | 85.18 | 87.06 | 87.48 | 12.52 | 2.54 |

TABLE 3

Evaluation of cytotoxicity of synthesized *N. oppositifolia* nanoparticles against MCF7 cell line with $IC_{50}$ = 19.2 µl/ml.

| Sample conc. (µl/ml) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 16.62 | 19.73 | 20.45 | 18.93 | 81.07 | 2.04 |
| 50 | 30.47 | 34.06 | 33.91 | 32.81 | 67.19 | 2.03 |
| 25 | 41.29 | 43.97 | 45.82 | 43.69 | 56.31 | 2.28 |
| 12.5 | 57.12 | 60.49 | 54.23 | 57.28 | 42.72 | 3.13 |
| 6.25 | 65.81 | 74.25 | 68.19 | 69.42 | 30.58 | 4.35 |
| 3.125 | 78.49 | 85.14 | 81.36 | 81.66 | 18.34 | 3.34 |

TABLE 4

Evaluation of cytotoxicity of synthesized *N. oppositifolia* nanoparticles against HepG-2 cell line with $IC_{50}$ = 21.9 µl/ml.

| Sample conc. (µl/ml) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 21.38 | 18.79 | 20.61 | 20.26 | 79.74 | 1.33 |
| 50 | 34.62 | 36.28 | 32.75 | 34.55 | 65.45 | 1.77 |
| 25 | 47.95 | 45.12 | 43.86 | 45.64 | 54.36 | 2.09 |
| 12.5 | 65.18 | 63.57 | 60.24 | 63.00 | 37.00 | 2.52 |
| 6.25 | 78.64 | 76.38 | 81.49 | 78.84 | 21.16 | 2.56 |
| 3.125 | 89.76 | 85.93 | 90.62 | 88.77 | 11.23 | 2.50 |

TABLE 5

Evaluation of cytotoxicity of synthesized N. oppositifolia nanoparticles against HCT-116 cells was detected with $IC_{50}$ = 10.9 µl/ml.

| Sample conc. (µl/ml) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 12.98 | 8.73 | 9.65 | 10.45 | 89.55 | 2.24 |
| 50 | 20.64 | 21.35 | 18.43 | 20.14 | 79.86 | 1.52 |
| 25 | 32.87 | 35.69 | 31.98 | 33.51 | 66.49 | 1.94 |
| 12.5 | 42.19 | 40.83 | 45.06 | 42.69 | 57.31 | 2.16 |
| 6.25 | 69.51 | 67.08 | 74.87 | 70.49 | 29.51 | 3.99 |
| 3.125 | 87.24 | 85.43 | 90.65 | 87.77 | 12.23 | 2.65 |
| 0 | 100 | 100 | 100 | 100 | 0.00 | |

Figure 10:
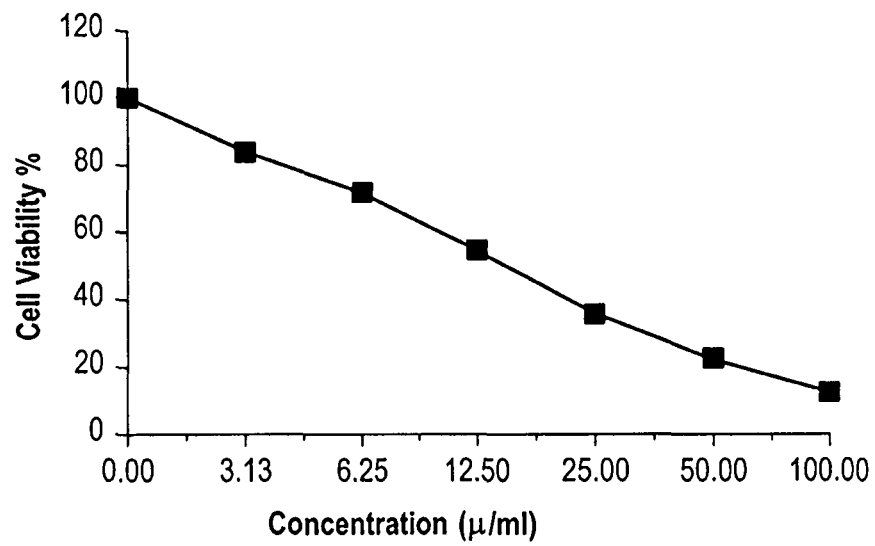
FIG. 10 is a graph showing the cytotoxicity of the *Nuxia oppositifolia* nanoparticles synthesized according to Example 2 of the present disclosure against MCF7 cell line.
Figure 11:
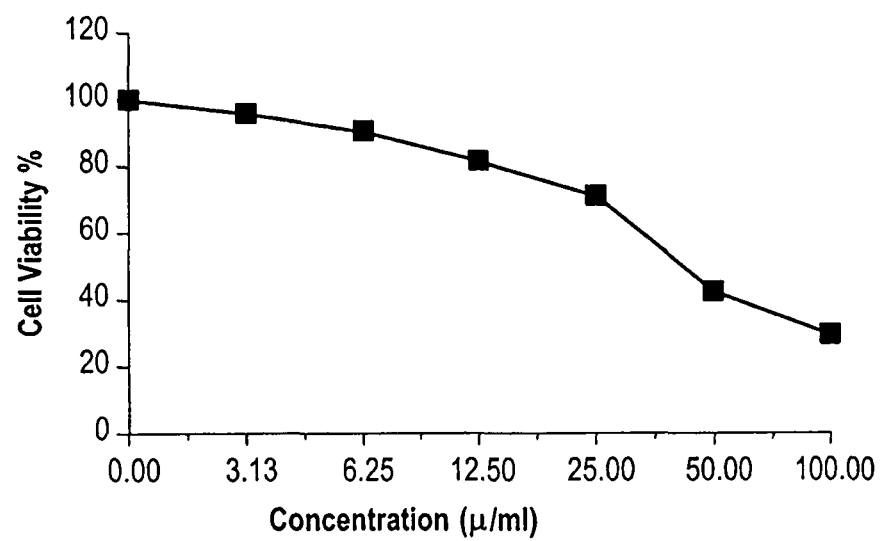
FIG. 11 is a graph showing the cytotoxicity of the *Nuxia oppositifolia* nanoparticles synthesized according to Example 2 of the present disclosure against hepatocellular carcinoma HepG-2 cell line.
Figure 12:
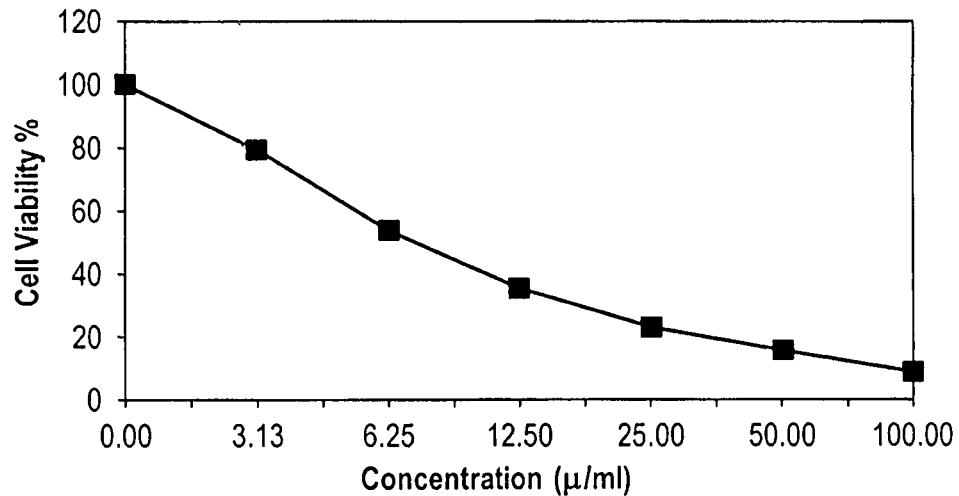
FIG. 12 is a graph showing the cytotoxicity of the *Nuxia oppositifolia* nanoparticles synthesized according to Example 2 of the present disclosure against human colon carcinoma HCT-116 cell line.
Figure 13:
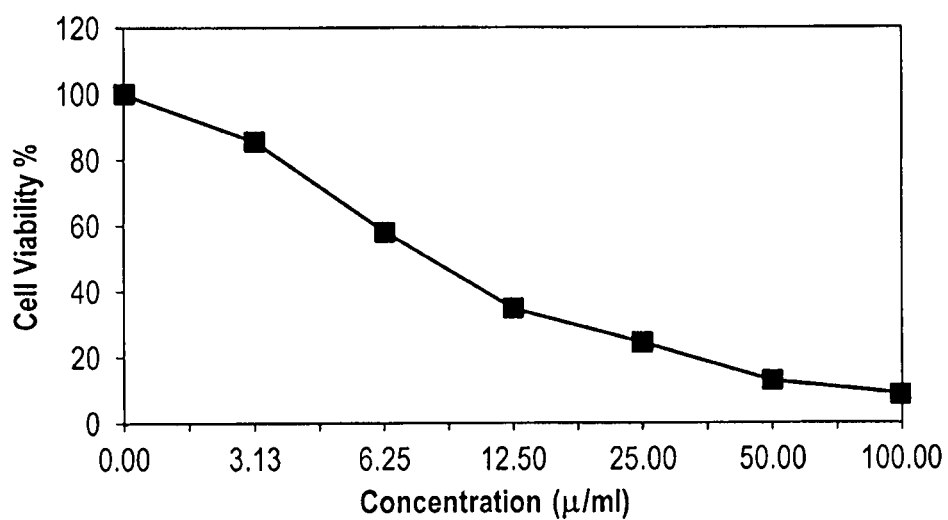
FIG. 13 is a graph showing the cytotoxicity of the *Nuxia oppositifolia* nanoparticles synthesized according to Example 2 of the present disclosure against human lung adenocarcinoma epithelial A549 cell line.
Figure 14:
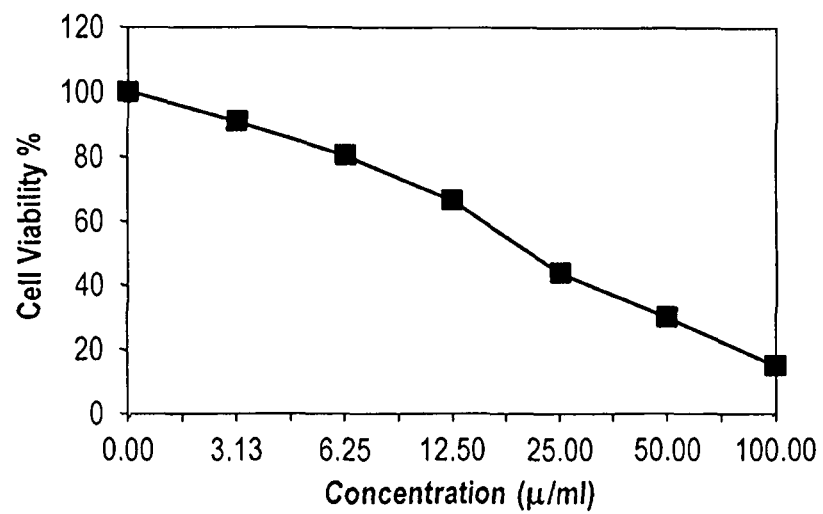
FIG. 14 is a graph showing the cytotoxicity of the *Nuxia oppositifolia* nanoparticles synthesized according to Example 2 of the present disclosure against cervical carcinoma cell line.

The cytotoxic effects of the nanoparticles synthesized according to Example 2 were evaluated against the five cancer cell lines, namely the breast carcinoma cells MCF-7 (FIG. 10, Table 6), the hepatocellular carcinoma cells HepG-2 (FIG. 11, Table 2), and the human colon carcinoma cells HCT-116 (FIG. 12, Table 3), the human lung adenocarcinoma epithelial cell line A549 (FIG. 13, Table 4), and the cervical carcinoma cells HELA (FIG. 14, Table 5). The results, provided in Tables 6-10 and FIGS. 10-14, indicate that the N. oppositifolia nanoparticles synthesized according to Example 2 are effective in inhibiting cancer cells.

TABLE 6

Evaluation of cytotoxicity of synthesized N. oppositifolia n-hexane extract nanoparticles against MCF-7 cell line with $IC_{50}$ = 15.7 µl/mL.

| Sample conc. (µl/mL) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 11.04 | 12.82 | 14.36 | 12.74 | 87.26 | 1.66 |
| 50 | 25.32 | 21.95 | 20.87 | 22.71 | 77.29 | 2.32 |
| 25 | 38.17 | 35.41 | 34.02 | 35.87 | 64.13 | 2.11 |
| 12.5 | 54.29 | 57.83 | 52.34 | 54.82 | 45.18 | 2.78 |
| 6.25 | 69.36 | 74.17 | 71.58 | 71.70 | 28.30 | 2.41 |
| 3.125 | 85.72 | 81.54 | 83.98 | 83.75 | 16.25 | 2.10 |

TABLE 7

Evaluation of cytotoxicity of synthesized N. oppositifolia n-hexane extract nanoparticles against HepG-2 cell line with $IC_{50}$ = 43.6 µl/mL.

| Sample conc. (µl/mL) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 29.86 | 27.96 | 30.81 | 29.54 | 70.46 | 1.45 |
| 50 | 46.43 | 38.71 | 42.96 | 42.70 | 57.30 | 3.87 |
| 25 | 73.69 | 70.83 | 69.28 | 71.27 | 28.73 | 2.24 |
| 12.5 | 82.31 | 81.95 | 80.64 | 81.63 | 18.37 | 0.88 |
| 6.25 | 90.64 | 89.67 | 91.53 | 90.61 | 9.39 | 0.93 |
| 3.125 | 95.78 | 94.32 | 97.16 | 95.75 | 4.25 | 1.42 |

TABLE 8

Evaluation of cytotoxicity of synthesized N. oppositifolia n-hexane extract nanoparticles against HCT-116 cell line with $IC_{50}$ = 7.63 µl/mL.

| Sample conc. (µl/mL) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 9.67 | 8.42 | 8.89 | 8.99 | 91.01 | 0.63 |
| 50 | 15.14 | 16.98 | 15.23 | 15.78 | 84.22 | 1.04 |
| 25 | 23.85 | 24.37 | 21.68 | 23.30 | 76.70 | 1.43 |
| 12.5 | 38.27 | 35.96 | 32.74 | 35.66 | 64.34 | 2.78 |
| 6.25 | 54.03 | 56.29 | 51.87 | 54.06 | 45.94 | 2.21 |
| 3.125 | 80.92 | 84.17 | 73.66 | 79.58 | 20.42 | 5.38 |

TABLE 9

Evaluation of cytotoxicity of synthesized N. oppositifolia n-hexane extract nanoparticles against A549 cell line with $IC_{50}$ = 8.47 µl/mL.

| Sample conc. (µl/ml) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 8.51 | 9.48 | 8.92 | 8.97 | 91.03 | 0.49 |
| 50 | 13.69 | 12.94 | 13.47 | 13.37 | 86.63 | 0.39 |
| 25 | 26.48 | 24.89 | 22.91 | 24.76 | 75.24 | 1.79 |
| 12.5 | 36.14 | 33.61 | 34.87 | 34.87 | 65.13 | 1.27 |
| 6.25 | 56.93 | 60.48 | 57.68 | 58.36 | 41.64 | 1.87 |
| 3.125 | 81.49 | 86.73 | 89.42 | 85.88 | 14.12 | 4.03 |

TABLE 10

Evaluation of cytotoxicity of synthesized n-hexane N. oppositifolia extract nanoparticles against Hela cell line with $IC_{50}$ = 21.7 µl/mL.

| Sample conc. (µl/mL) | % Viability (3 Replicates) | | | | % Inhibition | Standard Deviation (±) |
|---|---|---|---|---|---|---|
| | $1^{st}$ | $2^{nd}$ | $3^{rd}$ | Mean | | |
| 100 | 15.96 | 14.23 | 15.38 | 15.19 | 84.81 | 0.88 |
| 50 | 32.87 | 30.61 | 27.94 | 30.47 | 69.53 | 2.47 |
| 25 | 47.28 | 45.85 | 39.23 | 44.12 | 55.88 | 4.29 |
| 12.5 | 72.36 | 65.24 | 60.82 | 66.14 | 33.86 | 5.82 |
| 6.25 | 84.13 | 79.68 | 78.14 | 80.65 | 19.35 | 3.11 |
| 3.125 | 90.67 | 92.85 | 89.73 | 91.08 | 8.92 | 1.60 |

Example 4

Antimicrobial Activity Evaluation of *Nuxia oppositifolia* Nanoparticles

The antimicrobial effect of N. oppositifolia nanoparticles synthesized according to Example 1 were evaluated against gram positive bacteria, gram negative bacteria, as well as fungi. Results of the antimicrobial effect of the nanoparticles are provided in Table 6.

The antimicrobial effect of N. oppositifolia nanoparticles synthesized according to Example 2 were evaluated against gram positive bacteria, gram negative bacteria, as well as fungi. Results of the antimicrobial effect of the nanoparticles are provided in Table 11.

TABLE 6

Antimicrobial activity of synthesized *N. oppositifolia* nanoparticles using agar diffusion technique.

| Tested microorganisms | Sample Zone of Inhibition (±SD) | Reference Drug |
|---|---|---|
| Fungi | | Amphotericin B |
| *Absidi corymbifera* (RCMB 02564) | 21.3 ± 0.22 | 23.0 ± 0.10 |
| *Geotricum candidum* (RCMB 05097) | 23.0 ± 0.14 | 27.0 ± 0.20 |
| *Candida albicans* (RCMB 05036) | 20.3 ± 0.46 | 25.7 ± 0.10 |
| Gram Positive bacteria: | | Ampicillin |
| *Staphylococcus aureus* (RCMB 010027) | 24.0 ± 0.42 | 27.3 ± 0.14 |
| *Staphylococcus epidermidis* (RCMB 010024) | 25.3 ± 0.23 | 25.0 ± 0.18 |
| *Streptococcus pyogenes* (RCMB 010015) | 23.6 ± 0.89 | 26.3 ± 0.34 |
| Gram Negative bacteria: | | Gentamycin |
| *Proteous vulgaris* (RCMB 010085) | 23.6 ± 0.63 | 23.4 ± 0.30 |
| *Klebsiella pneumoniae* (RCMB 0010093) | 25.3 ± 0.12 | 26.4 ± 0.15 |
| *Salmonella enteritidis* (RCMB 010084) | 25.3 ± 0.68 | 25.2 ± 0.18 |

Data are expressed in the form of mean ± S.D. beyond well diameter (6 mm); 100 μl of samples were tested.

TABLE 11

Antimicrobial activities of synthesized *N. oppositifolia* n-hexane extract nanoparticles using agar diffusion technique

| Tested microorganisms | Sample Zone of Inhibition (±SD) | Reference drug |
|---|---|---|
| Fungi | | Amphotericin B |
| *Absidia corymbifera* (RCMB 02564) | 25.7 ± 0.44 | 23.0 ± 0.10 |
| *Geotricum candidum* (RCMB 05097) | 25.0 ± 0.58 | 27.0 ± 0.20 |
| *Candida albicans* (RCMB 05036) | 24.0 ± 0.42 | 25.7 ± 0.10 |
| Gram Positive bacteria | | Ampicillin |
| *Staphylococcus aureus* (RCMB 010027) | 26.0 ± 0.12 | 27.3 ± 0.14 |
| *Staphylococcus epidermidis* (RCMB 010024) | 29.0 ± 0.42 | 25.0 ± 0.18 |
| *Streptococcus pyogenes* (RCMB 010015) | 25.0 ± 0.15 | 26.3 ± 0.34 |
| Gram Negative bacteria | | Gentamycin |
| *Proteous vulgaris* (RCMB 010085) | 24.6 ± 0.34 | 23.4 ± 0.30 |
| *Klebsiella pneumoniae* (RCMB 0010093) | 27.8 ± 0.11 | 26.4 ± 0.15 |
| *Salmonella enteritidis* (RCMB 010084) | 27.0 ± 0.0 | 25.2 ± 0.18 |

Data are expressed in the form of mean ± S.D. beyond well diameter (6 mm); 100 μl of samples were tested It is to be understood that the synthesis of *Nuxia oppositifolia* nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing *Nuxia oppositifolia* nanoparticles, comprising the steps of:
   providing a *Nuxia oppositifolia* powder;
   dissolving the powder by maceration in 70% ethanol to provide a first ethanolic extract;
   filtering the ethanolic extract to obtain a filtrate;
   concentrating the filtrate from the ethanolic extract under pressure at 40° C. to provide a dried ethanolic extract;
   redissolving the dried ethanolic extract in 30% ethanol to provide a second ethanolic extract;
   successively partitioning the second ethanolic extract using n-hexane to provide a *Nuxia oppositifolia* n-hexane extract;
   dissolving the *Nuxia oppositifolia* n-hexane extract in methanol under stirring and water to provide a first solution;
   adding an effective amount of an acidic solution to the first solution to form a final solution including *Nuxia oppositifolia* nanoparticles; and
   centrifuging the final solution at 9000 rpm for 15 minutes to isolate and collect the *Nuxia oppositifolia* nanoparticles, wherein the nanoparticles have a particle size ranging from about 10 nm to about 200 nm.

2. The method of synthesizing *Nuxia oppositifolia* nanoparticles according to claim 1, wherein the acidic solution is hydrochloric acid solution.

3. The method of synthesizing *Nuxia oppositifolia* nanoparticles according to claim 1, wherein the *Nuxia oppositifolia* powder is prepared from dried, aerial parts of *N. oppositifolia*.

4. The method of synthesizing *Nuxia oppositifolia* nanoparticles according to claim 1, wherein the first ethanolic extract is concentrated using a rotary evaporator.

* * * * *